(12) United States Patent
Kantzer et al.

(10) Patent No.: US 11,242,310 B2
(45) Date of Patent: Feb. 8, 2022

(54) TWO-STEP PROCESS FOR CONVERTING CYCLIC ALKYLENE UREAS INTO THEIR CORRESPONDING ALKYLENE AMINES

(71) Applicant: NOURYON CHEMICALS INTERNATIONAL B.V., Arnhem (NL)

(72) Inventors: Eike Nicolas Kantzer, Uddevalla (SE); Karl Fredrik Lake, Södertälje (SE); Ina Ehlers, Stenungsund (SE); Stig Mikael Wernersson, Södertälje (SE); Rolf Krister Edvinsson, Partille (SE); Hendrik Van Dam, Ede (NL); Antoon Jacob Berend Ten Kate, Arnhem (NL); Rens Veneman, Amersfoort (NL); Michiel Jozef Thomas Raaijmakers, Deventer (NL); Slavisa Jovic, Utrecht (NL)

(73) Assignee: NOURYON CHEMICALS INTERNATIONAL B.V., Arnhem (NL)

( * ) Notice: Subject to any disclaimer, the term of this patent is extended or adjusted under 35 U.S.C. 154(b) by 0 days.

(21) Appl. No.: 16/638,395

(22) PCT Filed: Aug. 7, 2018

(86) PCT No.: PCT/EP2018/071322
§ 371 (c)(1),
(2) Date: Feb. 11, 2020

(87) PCT Pub. No.: WO2019/030193
PCT Pub. Date: Feb. 14, 2019

(65) Prior Publication Data
US 2020/0361850 A1    Nov. 19, 2020

(30) Foreign Application Priority Data
Aug. 11, 2017  (EP) .................................... 17185950

(51) Int. Cl.
C07C 209/62    (2006.01)
(52) U.S. Cl.
CPC .................................... C07C 209/62 (2013.01)
(58) Field of Classification Search
CPC ............................ C07C 209/62; C07C 209/86
See application file for complete search history.

(56) References Cited

U.S. PATENT DOCUMENTS

| | | | | |
|---|---|---|---|---|
| 2,436,311 A * | 2/1948 | Larson | .................. | C07D 233/34 548/326.1 |
| 2,514,380 A * | 7/1950 | Duschinsky | .......... | C10M 133/12 564/369 |
| 2,517,750 A * | 8/1950 | Wilson | .................. | C07D 233/32 548/313.7 |
| 2,812,333 A * | 11/1957 | Steele | .................... | C07D 233/32 548/323.5 |
| 2,825,732 A * | 3/1958 | Wayland, Jr. | ........ | C07D 233/34 548/323.5 |
| 3,073,800 A * | 1/1963 | Yim Poon | ............ | C08G 12/046 528/263 |
| 4,282,193 A * | 8/1981 | Melchior | ........... | B01D 53/1456 423/223 |
| 4,387,249 A * | 6/1983 | Hamden | ............... | C07C 209/62 564/488 |
| 4,503,250 A | 3/1985 | Herdle | | |
| 5,744,069 A * | 4/1998 | Maeda | .................... | C23F 11/10 252/389.61 |
| 10,428,010 B2 * | 10/2019 | Edvinsson | ............ | C07C 209/62 |
| 10,800,731 B2 * | 10/2020 | Veneman | ............. | C07D 263/20 |
| 2019/0047971 A1 * | 2/2019 | Edvinsson | ........... | C07D 295/13 |
| 2019/0308930 A1 * | 10/2019 | Kantzer | ................ | C07C 209/62 |
| 2020/0071260 A1 * | 3/2020 | Kantzer | ................ | C07C 213/02 |
| 2020/0165187 A1 * | 5/2020 | Ten Kate | .............. | C07C 209/86 |
| 2020/0165212 A1 * | 5/2020 | Raaijmakers | ......... | C07C 213/08 |
| 2020/0207701 A1 * | 7/2020 | Veneman | ............. | C07D 233/36 |
| 2020/0223800 A1 * | 7/2020 | Ten Kate | .............. | C07D 233/34 |
| 2020/0361851 A1 * | 11/2020 | Veneman | ............. | C07C 209/86 |
| 2020/0361873 A1 * | 11/2020 | Van Dam | ............. | C07C 209/70 |

FOREIGN PATENT DOCUMENTS

| | | | | |
|---|---|---|---|---|
| WO | WO-2017137529 A1 * | 8/2017 | ........... | C07C 209/62 |
| WO | WO-2019011709 A1 * | 1/2019 | ......... | C07D 295/125 |
| WO | WO-2019030189 A1 * | 2/2019 | ........... | C07C 209/62 |
| WO | WO-2019030193 A1 * | 2/2019 | ........... | C07C 213/02 |

OTHER PUBLICATIONS

G. Vasanthakumar et al., 37 Synthetic Communications, 2633-2639 (2007) (Year: 2007).*
EPO, European Extended Search Report issued in European Application No. 17185950.7, dated Jan. 11, 2018.
EPO, International Search Report and Written Opinion issued in International Application No. PCT/EP2018/071322, dated Nov. 20, 2018.
Kankaanpera, A. et al., "Ureas and amides as dipolar aprotic solvents in highly basic media. The dependence of kinetic basicity on solvent composition", Journal of the Chemical Society, Perkin Trans., 1999, pp. 169-174, vol. 2.

* cited by examiner

*Primary Examiner* — Alexander R Pagano
(74) *Attorney, Agent, or Firm* — Lorenz & Kopf, LLP

(57) ABSTRACT

A process is provided for converting cyclic alkyleneureas into their corresponding alkyleneamines. The process includes, in a first step, converting cyclic alkyleneureas into their corresponding alkyleneamines by reacting cyclic alkyleneureas in the liquid phase with water with removal of $CO_2$, so as to convert from about 5 mole % to about 95 mole % of alkyleneurea moieties in the feedstock to the corresponding amines. The process further includes, in a second step, adding an inorganic base and reacting cyclic alkylene ureas remaining from the first step with the inorganic base to convert them partially or completely into their corresponding alkyleneamines. Certain embodiments of the two-step process obtain a high conversion of cyclic alkyleneureas, while using substantially less strong inorganic base. Certain embodiments of the process process also show a higher selectivity to amines than prior art processes.

17 Claims, 1 Drawing Sheet

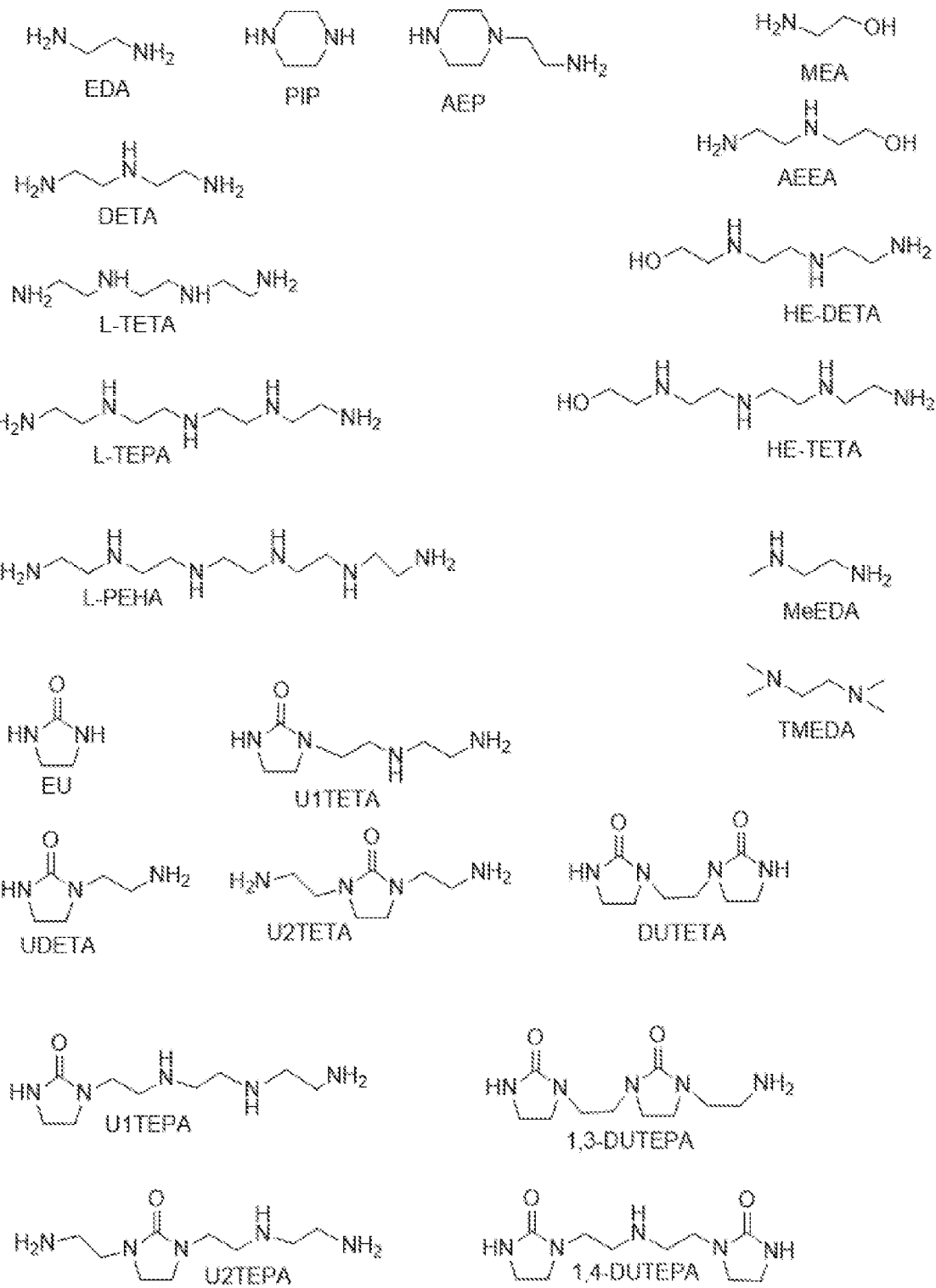
Chemical structures

TWO-STEP PROCESS FOR CONVERTING CYCLIC ALKYLENE UREAS INTO THEIR CORRESPONDING ALKYLENE AMINES

CROSS-REFERENCE TO RELATED APPLICATION

This application is a U.S. National-Stage entry under 35 U.S.C. § 371 based on International Application No. PCT/EP/2018/071322, filed Aug. 7, 2018, which was published under PCT Article 21(2) and which claims priority to European Application No. 17185950.7, filed Aug. 11, 2017, which are all hereby incorporated in their entirety by reference.

TECHNICAL FIELD

The present invention pertains to a process for converting cyclic alkylene ureas into their corresponding alkylene amines, in particular to a two-step process.

BACKGROUND

Cyclic alkyleneureas are compounds comprising two nitrogen atoms connected by a carbonyl moiety and an alkylene moiety. For example, cyclic ethyleneurea is a compound comprising a cyclic ethyleneurea moiety in which two nitrogen atoms are connected by a carbonyl moiety and an ethylene moiety, in accordance with the following formula:

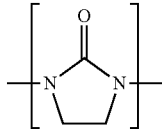

Cyclic alkyleneurea compounds can be converted into the corresponding alkyleneamines by removal of the CO group and addition of two hydrogen atoms.

Alkyleneamines, in particular ethyleneamines, specifically in particular diethylene triamine (DETA) and higher ethyleneamines such as (linear) triethylene tetramine (L-TETA) are attractive products from a commercial point of view. Cyclic ethyleneureas are therewith an attractive precursor in the manufacture of ethylenediamine and higher ethyleneamines.

It has been found, however, that cyclic alkyleneureas are relatively stable and difficult to convert to the corresponding alkyleneamines. This can also be seen from the prior art, where the conversion is carried out with large excesses of strong inorganic bases. The difficulty in converting cyclic alkyleneureas into the corresponding alkyleneamines using strong inorganic bases goes in particular for compounds where the alkyleneurea moiety is connected to further alkyleneamine moieties via the nitrogen atoms, in particular where the alkyleneurea moiety is present between two further alkyleneamine moieties.

U.S. Pat. No. 4,503,250 describes a process for preparing linear polyalkylene polyamines which comprises reacting ammonia or an alkyleneamine compound having two primary amino groups or mixtures thereof with an alcohol or an alkanolamine compound having a primary amino group and a primary or secondary hydroxyl group or mixtures thereof in the presence of a derivative of carbonic acid at a temperature at which the reaction will proceed under pressures sufficient to maintain the reaction mixture substantially in a liquid phase. The process results in the formation of urea adducts of polyalkylene polyamines. The urea adducts are converted to polyethylene polyamines by reaction with 50% aqueous KOH under reflux overnight. 8 moles KOH are used per mole carbon dioxide.

U.S. Pat. No. 4,387,249 discloses the reaction of ethylenediamine (EDA), ethanolamine (MEA) and urea to give aminoethylethyleneurea (UDETA) and ethyleneurea (EU), which are hydrolysed to form DETA and EDA. The hydrolysis step takes place in an inert atmosphere in the presence of a Brønsted base. The Brønsted base preferably is the hydroxide of an alkali metal, more preferably an aqueous solution of NaOH. In the examples hydrolysis takes place at a temperature of 200° C. under autogenous pressure, using a 5 mole/liter NaOH solution.

While quite effective, the process as described in these references has a number of disadvantages. The use of caustic bases has as a disadvantage that it results in low product selectivities due to degradation of the desired products. In addition, when using an (inorganic) base, salts are formed as by-products which complicate the following separation of organics, resulting in lower yields of the targeted product. In addition the combination of amines, water, salt and high temperatures can cause problems with corrosion, discolored products and decreased storage stability. Further, an outlet has to be found for processing the large amounts of salts.

Other methods for converting ethyleneurea compounds into the corresponding ethyleneamines have also been described. They are, however, not very effective. Kankaanpera et al (J. Chem. Soc. Perkin Trans 2, 1999, 169-174) describes the use of water containing 0.02 mole NaOH per liter at 25° C. For cyclic 1,3-dimethylimidazolidin-2-one a half-life of 5 days is reported.

U.S. Pat. No. 2,812,333 describes the hydrolysis of 1-(2-hydroxyethyl) imidazolidone-2 to N-(2-hydroxyethyl)ethylenediamine with water under the removal of CO2. In Example 2, the reaction is carried out on a 12% solution of 1-(2-hydroxyethyl) imidazolidone in water at a temperature of 175° C. in a sealed autoclave. The rate of hydrolysis is 5% of the compound per hour.

There is need in the art for a process for converting cyclic alkylene ureas into their corresponding alkylene amines which shows a high conversion of cyclic alkylene ureas into the corresponding alkyleneamines and which can be operated in an efficient manner. The present invention provides such a process.

BRIEF SUMMARY

A process is provided for converting cyclic alkyleneureas into their corresponding alkyleneamines. The process includes in a first step, converting cyclic alkyleneureas into their corresponding alkyleneamines by reacting cyclic alkyleneureas in the liquid phase with water with removal of CO2, so as to convert from about 5 mole % to about 95 mole % of alkyleneurea moieties in the feedstock to the corresponding amines. Further, the process includes, in a second step, adding an inorganic base and reacting cyclic alkylene ureas remaining from the first step with the inorganic base to convert them partially or completely into their corresponding alkyleneamines.

Surprisingly it has been found that the two-step process of the present invention makes it possible to still obtain a high conversion and yield of cyclic alkyleneureas, while using substantially less inorganic base. The use of less inorganic base consequentially leads to further advantages like less salt formation and less corrosion. The process according to the invention also shows a higher selectivity to amines than the prior art process. Further advantages of the process according to the invention and specific embodiments thereof will become apparent from the further specification.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter. The process is described in more detail below.

BRIEF DESCRIPTION OF THE DRAWINGS

The present invention will hereinafter be described in conjunction with the following drawing FIGURE, wherein like numerals denote like elements, and:

FIG. 1 illustrates the molecular structures of some cyclic alkyleneureas.

DETAILED DESCRIPTION

The following detailed description is merely exemplary in nature and is not intended to limit the invention or the application and uses of the invention. Furthermore, there is no intention to be bound by any theory presented in the preceding background of the invention or the following detailed description.

In certain embodiments, numbers in this description indicating amounts, ratios of materials, physical properties of materials, and/or use are may be understood as being modified by the word "about". The term "about" as used in connection with a numerical value and the claims denotes an interval of accuracy, familiar and acceptable to a person skilled in the art. In general, such interval of accuracy is ±10%.

The starting material used in the present invention is a reaction mixture comprising cyclic alkyleneureas. Cyclic alkyleneureas are compounds comprising two nitrogen atoms connected by a carbonyl moiety and an alkylene moiety. For example, in a cyclic ethyleneurea, two nitrogen atoms are connected through a carbonyl moiety and an ethylene moiety in accordance with the following formula:

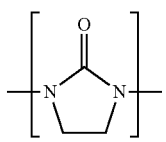

In a preferred embodiment in the process of the invention the cyclic alkyleneurea that is subjected to the conversion to give a corresponding alkyleneamine are:

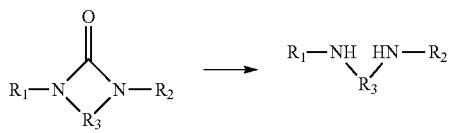

Wherein $R_1$ and $R_2$ each independently are chosen from the group of hydrogen, an alkyleneamine group of the formula $X-R_3-(NH-R_3-)_p-$, or an alkoxy group of formula $X-R_3-(O-R_3-)_n-$, or a group combining such alkyleneamine and alkoxy units p and n, wherein one or more units $\sim N-R_3-N\sim$ may be present as either one of the rings

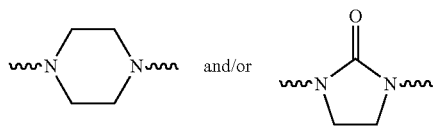

and wherein each $R_3$ independently is as defined below and X may be hydroxyl, amine, a linear or branched C1-C20 hydroxyalkyl or C1-C20 aminoalkyl group, n and p independently is at least 0, preferably 1-20, more preferably 2-20, optionally containing one or more piperazine, or alkyleneurea groups, or when p or n is 0 may be a C1-C20 hydroxyalkyl or C1-C20 aminoalkyl, and $R_3$ is alkylene or substituted alkylene.

In a preferred embodiment R2 is a hydrogen atom and R1 is not a hydrogen atom.

In a more preferred embodiment R2 is a hydrogen atom and R1 is a group that may contain a repeating alkyleneamine group, even more preferably a repeating ethyleneamine group of the formula $X-(NH-C_2H_4)_n$ wherein optionally one or more units $-NH-C_2H_4-NH-$ may be present as one of the rings

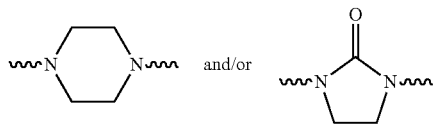

and wherein n is 0 to 20, and X may be a hydrogen atom, an aminoalkyl, an hydroxyalkyl, N-imidazolidinonealkyl or piperazinoalkyl group, most preferably wherein the alkyl is ethyl.

R3 is preferably ethylene or propylene, optionally substituted with C1-C3 alkyl substituents. More preferably it is an unsubstituted ethylene, unsubstituted propylene or isopropylene, most preferably an unsubstituted ethylene.

Some examples of cyclic alkylene ureas that are most preferred are EU (ethyleneurea), UDETA (the urea of diethylenetriamine), UTETA (the ureas of triethylenetetraamine, i.e. U1TETA or U2TETA, dependent on whether the urea is between the $1^{st}$ and $2^{nd}$ amine in the chain or $2^{nd}$ and $3^{rd}$ amine, respectively), DUTETA (the diurea of triethylenetetramine), UTEPA (the ureas of tetraethylenepentamine, i.e. U1TEPA, U2TEPA depending on where the urea unit is located), DUTEPA (DU1,3TEPA, DU1,4TEPA, the diureas of tetraethylenepentamine), UAEEA (the urea of aminoethylethanolamine), HE-UDETA (the urea of hydroxyethyl diethylenetriamine, that can exist in two isomers HE-U1DETA and HE-U2DETA), HE-UTETA (the urea of hydroxyethyl triethylenetetraamine, that can exist in three isomers HE-U1TETA, HE-U2TETA and HE-U3TETA), HE-DUTETA (the diurea of hydroxyethyl triethylenetetraamine), or any mixture of these. The molecular structures of a number of the above cyclic alkylene ureas are given in FIG. 1. To avoid any confusion, if a number is given for the amine group where the cyclic urea unit U is located, the amine groups are counted from the terminal amine group on the molecule which in the case of hydroxyethylated ethylene amines is the amine group at the end not containing the hydroxyl group.

The process according to the invention is particularly suitable for converting mixtures of alkyleneamines comprising at least 10 mole % of cyclic urea derivatives of alkyleneamine compounds comprising a —NH—R3-NH—R3-NH—R3-NH— moiety, calculated on the total of cyclic urea compounds present in the mixture. Cyclic urea derivatives of compounds having this moiety are relatively difficult to convert into the corresponding amines, and it is a feature of the process of the present invention that mixtures comprising these compounds can be converted while obtaining a high yield. It may be preferred for the starting material to be a mixture of alkyleneamines comprising at least 15 mole %, in particular at least 20 mole %, of cyclic urea derivatives of alkyleneamine compounds comprising a —NH—R3-NH—R3-NH—R3-NH— moiety, calculated on the total of cyclic urea compounds present in the mixture.

In the first step of the process according to the invention a feedstock comprising cyclic alkyleneureas is reacted in the liquid phase with water, optionally with an amine compound selected from the group of primary amines, cyclic secondary amines, and bicyclic tertiary amines, so as to convert between 5 mole % and 95 mole % of alkyleneurea moieties in the feedstock to the corresponding amines.

It is a key feature of the present invention that in the first step of the process according to the invention, part but not all of the cyclic alkyleneurea moieties are converted into the corresponding alkyleneamine moieties. As it is not necessary to obtain full conversion of cyclic alkyleneurea moieties in the first step, the reaction conditions in the first step can be kept relatively mild, and the reaction time relatively short. This also prevents the formation of side products.

In the first step of the process according to the invention, between 5 and 95 mole % of the cyclic alkyleneurea moieties in the starting material will be converted into the corresponding amine moieties. Depending on the composition of the starting material and the reaction conditions in the first step, the percentage of cyclic alkyleneurea moieties converted may vary. To obtain an efficient process, a skilled person will be able to, for example, select the proper total amount of compounds, their concentrations and their relative ratios in the starting material.

It is considered preferred for at least 30 mole % of the cyclic ethylene urea moieties in the starting material to be converted in the first step. It may be preferred for at most 95 mole % of the cyclic ethylene urea moieties in the starting material in the first step, in particular at most 90 mole % of cyclic ethylene urea moieties.

In one embodiment of the present invention, the product from the first step is provided in its entirety to the second step. In another embodiment of the present invention, amine compounds generated in the first step are removed from the reaction mixture during the first step, or between the first step and the second step. The latter option may be preferred, as this will limit the volume to be provided to the second step.

The removal of amines between the first and second step can be carried out, e.g., through distillation or other separation methods.

The various steps of the process according to the invention will be discussed in more detail below.

The First Step

In the first step of the process according to the invention, cyclic alkyleneureas are converted into their corresponding alkyleneamines by reacting cyclic alkyleneureas in the liquid phase with water with removal of $CO_2$, so as to convert between 5 mole % and 95 mole % of alkyleneurea moieties in the feedstock to the corresponding amines. This step is also indicated herein as the $CO_2$ removal step.

The reaction with water generally takes place at a temperature of at least 150° C. If the reaction temperature is below 150° C., the cyclic ethylene ureas will not react to a significant extent. It is preferred for the reaction to be carried out at a temperature of at least 180° C., in particular at least 200° C., more in particular at least 230° C., or even at least 250° C. Preferably the temperature during this step does not exceed 400° C., in particular at most 350° C., more in particular at most 320° C.

The pressure during the process is not critical, as long as the reaction medium is in the liquid phase. As a general range, a value of 0.5 to 100 bar may be mentioned, depending on the desired temperature. It is preferred for the $CO_2$ removal step to be carried out at a pressure of at least 5 bar, in particular at least 10 bar, to maintain a sufficient amount of amine and water in the medium. In view of the high costs associated with high-pressure apparatus, it may be preferred for the pressure to be at most 50 bar, in particular at most 40 bar.

The amount of water depends on the desired degree of conversion and on the process conditions. In general, the amount of water is at least 0.1 mole water per mole urea moiety in the feedstock. Higher amounts are often used, e.g., at least 0.1 mole water per mole urea moiety, in particular at least 0.5 mole water per mole urea moiety. The maximum is not critical for the process according to the invention but too large amounts of water will lead to unnecessarily large equipment being required. As a general maximum an amount of at most 500 mole water per mole cyclic ethylene urea moiety may be mentioned, in particular at most 300 mole, more in particular at most 200 mole, in some embodiments at most 100 mole, or at most 50 mole.

$CO_2$ removal can be carried out when the conversion of the alkyleneureas into ethyleneamine compounds using water has been completed. However, it is preferred to carry out $CO_2$ removal during the conversion reaction. $CO_2$ removal can be carried out in manners known in the art. The most basic way to do this is to vent the reaction vessel. A stripping fluid, in particular a stripping gas can be used to increase $CO_2$ removal rate. Other measures to improve removal of $CO_2$ will be evident to the skilled person, and include measures like stirring of the reaction mixture, sparging of stripping gas, thin-film evaporation, use of packing or trays, etc.

Where a stripping gas is used, the flow rate is typically at least 1 m3 per 1 m3 reactor volume per hour (at reaction temperature and pressure), and at most 100 m3 per 1 m3 reactor volume per hour (at reaction temperature and pressure). The stripping flow rate can be generated by evaporation of a liquid inside the reactor vessel, resulting in in situ generation of stripping gas. The ranges above also apply to this embodiment. Of course, it is also possible to combine the addition of tripping gas with the in situ formation of stripping gas. The $CO_2$-containing stripping fluid removed from the $CO_2$ removal step can, for example, comprise from 1 to 99 mol. % $CO_2$. In other embodiments, the stripping fluid may comprise 1-80 mol. % $CO_2$, or 1-60 mol. % $CO_2$. In some embodiments, the effluent from the $CO_2$ removal step may comprise 1-40 mol. % $CO_2$, or 1-20 mol. % $CO_2$. Lower $CO_2$ contents make for more efficient stripping, but also for the use of more stripping gas. It is within the scope of the skilled person to find an appropriate balance between these parameters.

Depending on the reaction temperature and the desired degree of conversion, the reaction time can vary within wide ranges, e.g., at least one minute, in particular at least 5 minutes, more in particular between 15 minutes and 24 hours. In one embodiment, the reaction time may be at least 30 minutes, or at least 1 hour. It may be preferred for the reaction time to vary between 1 hour and 12 hours, in particular between 1 hour and 6 hours. When using lower temperatures, longer reaction times may be required to obtain the desired degree of conversion.

The conversion with water does not rely on the use of an inorganic base. Nevertheless, if so desired, a limited amount of inorganic base may be present. Within the context of the present invention, an inorganic base is a Lewis or Brønsted base which does not contain carbon-carbon bonds. In many embodiments the inorganic base contains a metal, alkali-metal or alkaline earth metal cation, and in many embodiments it is a Brønsted base. Preferably the inorganic base is a strong inorganic base is a material which does not contain carbon-carbon bonds and which has a pKb of less than 1. In one embodiment, the strong inorganic base, if used, is selected from the group of metal hydroxides, in particular from the group of hydroxides of alkaline and earth alkaline metals, in particular from sodium hydroxide, potassium hydroxide, lithium hydroxide, calcium hydroxide, magnesium hydroxide, and barium hydroxide. In one embodiment, the strong inorganic base is selected from the group of metal oxides, in particular from the group of oxides of alkaline and earth alkaline metals, in particular from calcium oxide, magnesium oxide, and barium oxide. Selecting a strong inorganic base from the group of sodium hydroxide, potassium hydroxide, magnesium (hydr)oxide, and calcium (hydr)oxide may be preferred. The use of sodium hydroxide and potassium hydroxide may be particularly preferred. Other strong inorganic bases may also be used, such as ammonium hydroxide. As will be evident to the skilled person, mixtures of various (strong) inorganic bases can be used. Compounds comprising a strong base in addition to other components can also be used, as can be compounds which will be converted into strong inorganic bases in the reaction medium. If a (strong) inorganic base is used, it is generally used in an amount of less than 0.5 mole inorganic base per mole cyclic alkyleneurea moieties, in particular less than 0.2 mole inorganic base per mole cyclic alkyleneurea moieties. It will be evident to the skilled person that the amount of inorganic base present in the first step, calculated on the number of alkyleneurea moieties present at the start of the first step, is smaller than the amount of inorganic base present in the second step, calculated on the number of alkyleneurea moieties present at the start of the second step.

In one embodiment of the present invention, the $CO_2$ removal step is carried out by reacting cyclic alkyleneureas in the liquid phase with water in an amount of 0.1-20 mole water per mole urea moiety, at a temperature of at least 230° C., with removal of $CO_2$. It has been found that the use of a low amount of water in combination with a relatively high temperature and $CO_2$ removal results in an efficient process which good conversion and low formation of side products.

It has been found that it is possible in this embodiment of the process according to the invention to obtain good conversion with the relatively limited amount of water of at most 20 mole water per mole urea moiety. It has been found that it is possible to work at even lower amounts of water, e.g., and amount of at most 15 mole water per mole urea moiety, more in particular an amount of at most 10 mole water per mole urea moiety, or even at most 5 mole water per mole urea moiety.

The range of 0.1-20 mole water per mole urea moiety refers to the entire amount of water added during the process, calculated on the amount of urea moieties in feedstock at the start of the reaction. To obtain full conversion, 1 mole water is required per mole urea moiety to be converted. As full conversion is not always necessary, lower amounts of water may be possible. Therefore, water is used in an amount of at least 0.1 mole per mole urea moiety. Higher amounts are often used, e.g., at least 0.2 mole per mole urea moiety, in particular at least 0.5 mole water per mole urea moiety.

Water can be added at the beginning of the process in a single dosing. It is preferred, however, to add the water during the process, in several dosings or continuously. In a continuous operation multiple feedpoints may be used. By matching the amount of water added to the amount of water consumed by the reaction, the excess water in the reaction mixture can be limited. It has been found that this limits the formation of side products.

The molar ratio of water to urea moieties is calculated on the water present in the liquid reaction medium. If water is added in the form of steam, which may be an attractive embodiment to combine water addition with the provision of heat to the reaction mixture, the majority of water in the steam will not be absorbed in the liquid reaction medium. It is within the scope of the skilled person to regulate the conditions of a water addition process via stream in such a way that the desired amount of water is absorbed by the reaction medium. The water can also be present in the feedstock from the beginning of the reaction, e.g., as a result of the process by which the feedstock was produced. Water can also be added as a liquid.

In this embodiment of the present invention with removal of $CO_2$, the reaction is performed at a temperature of at least 230° C. It has been found that at a temperature below this value, the reaction rate is too low to obtain meaningful conversion in an acceptable time frame. It is preferred to carry out the reaction at a temperature of at least 240° C., in particular at least 250°. As a maximum value, a value of 400° C. may be mentioned. It may be preferred to carry out the reaction at a temperature of at most 350° C., in particular at most 320° C.

In this embodiment of the present invention the pressure is not critical, as long as the reaction medium is in the liquid phase. As a general range, a value of 0.5 to 100 bar may be mentioned. For preferred pressure ranges reference is made to what has been stated above.

As indicated above, in one embodiment of the present invention the first step of the process according to the invention is carried out in the presence of an amine compound selected from the group of primary amines, cyclic secondary amines, and bicyclic tertiary amines.

Primary amines are amine functional compounds in which the amine group is of the formula R4-$NH_2$ and wherein R4 can be any organic group, preferably an aliphatic hydrocarbon with optional heteroatoms such as oxygen and/or nitrogen. Secondary cyclic amines are amines of the formula R5-NH—R6, wherein R5 and R6 together form a hydrocarbon ring, optionally with heteroatoms such as oxygen and/or nitrogen, preferably a piperazine ring. Tertiary bicyclic amines are amines of the formula R7-N(—R9)-R8 where R7 and R8 together form a hydrocarbon ring—optionally with heteroatoms such as oxygen and/or nitrogen—and R7 and R9 together form another hydrocarbon ring—optionally with heteroatoms such as oxygen and/or nitrogen. On all the above groups R4 to R9 substituents can be present, like alkyl or hydroxyalkyl groups. Primary amines, cyclic secondary amine and bicyclic tertiary amines all contain a sterically relatively unhindered amine group. In this document a compound is defined as a primary amine or a secondary cyclic amine or a tertiary bicyclic amine if one of the amine groups in the compound is a primary amine or secondary cyclic amine or a tertiary bicyclic amine group, independent of if this compound contains further amine groups that may be different in their nature. A compound can also contain two or more different amine functionalities, e.g. a primary amine and a secondary cyclic amine functionality or a primary amine, a secondary cyclic amine and a tertiary bicyclic amine functionality.

Preferred examples of primary amines are alkylamines, linear ethylene amines, and alkanolamines. Preferred examples of cyclic secondary amines are amines that contain a terminal piperazine ring. Preferred examples of bicylic tertiary amines are 1,4-diazabicyclo[2.2.2]octane (DABCO), 1,4-diazabicyclo[2.2.2]octan-2-yl)methanol and 1-azabicyclo[2.2.2]octane (Quinuclidine).

The amine compound is preferably a compound with more than one amine group wherein at least one of the amine groups is a primary amine, even more preferably it is an amine wherein two amine groups are a primary amine. The amine compound is preferably a compound different than R1-NH—R3-NH—R2 that is obtained by the process of the invention. In another preferred embodiment the amine compound is a compound that can bind with the carbonyl group from the cyclic ethylene urea. Preferred amine compounds include an alkylene amine, or an alkanol amine compound, even more preferably a smaller alkylene amine, ethylene amine, or alkanol amine, ethanolamine, than is formed by the process of the invention, most preferably ethylenediamine (EDA), diethylenetriamine (DETA), monoethanolomine (MEA), aminoethylethanolamine (AEEA), N-aminoethylpiperazine (AEP), N, N'-diaminoethylpiperazine (DAEP), UDETA, N,N'-diaminoethyl-2-imidazolidinone (U2TETA), tris-aminoethylamine (TAEA).

In yet another preferred embodiment the amine compound is a compound that binds the carbonyl group from the cyclic alkylene urea to give among others another linear or cyclic alkylene urea or linear or cyclic alkylene carbamate, that is larger or less volatile than the alkylene amine formed by the process of the invention, even more preferably an ethylene amine that is solid under the conditions used to work up the reaction mixture or an ethylene amine bound to a solid carrier. Examples thereof are DETA-PS (i.e. a diethylene triamine linked to a solid polystyrene) or a solid polyethyleneimine (PEI).

Preferred amine compounds that can be used in the CO2 removal step of the process according to the invention include ethylenediamine (EDA), N-methylethylenediamine (MeEDA), diethylenetriamine (DETA), ethanolamine (MEA), aminoethylethanolamine (AEEA), piperazine (PIP), N-aminoethylpiperazine (AEP), 1,4-diazabicyclo[2.2.2]octane (DABCO), 1,4-diazabicyclo[2.2.2]octan-2-yl)methanol, triethylenetetramine (TETA), N-diethyldiamine-2-imidazolidinone (U1TETA), N, N'-diaminoethylpiperazine (DAEP), N-[(2-aminoethyl)2-aminoethyl]piperazine) (PEEDA), the cyclic urea of PEEDA (UPEEDA), N, N'-diaminoethyl-2-imidazolidinone (U2TETA), tetraethylenepentamine (TEPA), pentaethylenehexamine (PEHA), and the mono cyclic ureas of TEPA and PEHA (i.e. U1TEPA, U2TEPA, U1PEHA, U2PEHA, U3PEHA) and the dicyclic urea isomers of PEHA (i.e. DUPEHA), a polyethyleneimine (PEI) or an alkylene amine on a solid carrier.

The amine compound, if used, is preferably dosed in a molar amount of between 0.001 and 100 equivalents in regard to the total molar amount of cyclic ethylene urea, more preferably between 0.01 and 50 equivalents, even more preferably between 0.05 and 30 equivalents, yet more preferably between 0.15 and 25 equivalent and most preferably between 0.20 and 20 equivalents.

The reaction with water in the presence of an amine in the CO2 removal step is preferably carried out at a temperature of at least 150° C., preferably at least 200° C., more preferably at least 230° C., and most preferably of at least 250° C. Preferably the temperature during the process does not exceed 400° C., more preferably 350° C.

The reaction with water and amine compound in one embodiment of the first step of the process according to the invention is generally performed for a time of between 1 minute and 12 hours. Preferably the reaction is run in less than 10 hours, more preferably in less than 8 hours, most preferably less than 5 hours. As a skilled person will understand this reaction time does not include any further processing of the reaction mixture such as for separating the obtained compounds.

As discussed above, if so desired the CO2 removal step can be carried out with water in the presence of an amine compound selected from the group of primary amines, cyclic secondary amines, and bicyclic tertiary amines.

In a preferred embodiment, in the first step of the process according to the invention a cyclic ethylene urea of TETA or TEPA, such as linear TETA diurea (DUTETA) or linear TEPA diurea (DUTEPA), is converted to linear TETA (L-TETA) or linear TEPA (L-TEPA) by employing an amine selected from the group of EDA, DETA, MEA, AEEA, N-methyl-EDA (MeEDA), AEP, DAEP, PEEDA, U2TETA, and TAEA. Particularly preferred are the amine compounds EDA, DETA, U2TETA, DAEP, PEEDA or AEP. The conversion of DUTETA with EDA and water proceeds preferably between 150 and 350° C., preferably between 200 and 300° C.

In the CO2 removal step, CO2 is removed from the system. The system comprises other volatile compounds such as water and in some embodiments low-boiling amines. The CO2 removal step focuses on the removal of CO2, and while evaporation of other volatiles may not be detrimental, it will generally be limited. This can, e.g., be done by the use of a (partial) condenser.

It is preferred for the composition provided to the first step to consist for at least 70 wt. % of the total of water, cyclic alkylene ureas, in particular those indicated above as preferred, and if present, amine compounds selected from the group of primary amines, cyclic secondary amines, and bicyclic tertiary amines, in particular those indicated above as preferred. It is particularly preferred for the composition provided to the first step to consist for at least 80 wt. % of the total of these compounds, more in particular for at least 90 wt. %.

The Second Step

In the second step of the process according to the invention, the product from the first step, with or without intermediate removal of amine compounds, is subjected to a treatment with a strong inorganic base. If so desired, only part of the product from the first step is subjected to a treatment with a strong inorganic base. Of course, it is also possible to also provide other compositions containing cyclic alkyleneureas to the treatment with strong inorganic base, so that a combined composition is subjected to treatment with strong inorganic base.

Within the context of the present invention, a strong inorganic base is a base with a material which does not contain carbon-carbon bonds and which has a pKb of less than 1.

In one embodiment, the strong inorganic base is selected from the group of metal hydroxides, in particular from the group of hydroxides of alkaline and earth alkaline metals, in particular from sodium hydroxide, potassium hydroxide, lithium hydroxide, calcium hydroxide, magnesium hydroxide, and barium hydroxide. In one embodiment, the strong inorganic base is selected from the group of metal oxides, in particular from the group of oxides of alkaline and earth alkaline metals, in particular from calcium oxide, magnesium oxide, and barium oxide. Selecting a strong inorganic base from the group of sodium hydroxide, potassium hydroxide, magnesium (hydr)oxide, and calcium (hydr)oxide may be preferred. The use of sodium hydroxide and potassium hydroxide may be particularly considered preferred. Other strong inorganic bases may also be used, such as ammonium hydroxide. As will be evident to the skilled person, mixtures of various strong inorganic bases can be used. Compounds comprising a strong base in addition to other components can also be used, as can be compounds which will be converted into strong inorganic bases in the reaction medium.

The lower limit of the molar ratio of inorganic base to cyclic alkyleneurea moieties is not critical. A value of at least 0.2:1 may be mentioned. If it is desired to obtain full or near full conversion of the cyclic alkyleneurea moieties into the corresponding alkyleneamine, the use of larger amounts may be preferred, e.g., in a molar ratio of at least 0.5:1, in particular at least 1:1. It may be preferred to use larger amounts to increase the reaction rate, e.g., a molar ratio of inorganic base to cyclic alkyleneurea of at least 1.5:1, in particular at least 2:1, in some embodiments at least 2.5:1.

As large amounts of base do not contribute to further conversion but will lead to additional costs, it is preferred for the molar ratio of the inorganic base to the molar amount of cyclic ethylene urea moieties in the product provided to the treatment with the inorganic base to be at most 20:1, in particular at most 15:1, more in particular at most 10:1. It has been found that even lower amounts of inorganic base can suffice. More in particular, it has been found that good results can be obtained at a molar ratio of inorganic base to cyclic alkyleneurea moieties of at most 7.5:1, in particular at most 6.5:1, even more in particular at most 5.5:1. It has been found that the use of a molar ratio of at most 5.5:1 results in full conversion of the cyclic alkyleneurea moieties and high yield of the resulting alkyleneamines. It may be preferred to use even less inorganic base per mole of ethyleneurea, e.g., in a more ratio of at most 5:1, in particular at most 4:1, in some embodiments at most 3:1. The molar ratio is calculated on the molar amount of cyclic urea moieties in the feed provided to the caustic treatment step.

The treatment with inorganic base can, for example, be carried out by contacting the material to be treated, with a concentrated aqueous solution of the inorganic base. Depending on the nature of the base and the further composition of the reaction mixture, it may also be possible to add the base in solid form and suspend and or to (partially) dissolve it in the reaction medium. As will be clear to the skilled person, the aim is to bring the base in a dissolved state, so that the hydroxyl groups can react with the urea moieties, while avoiding unnecessary dilution of the reaction medium.

The reaction can be carried out at a temperature between room temperature and 400° C. The temperature and pressure should be selected such that the reaction mixture is in the liquid phase. Higher temperatures are advantageous because they lead to decreased reaction times. It may be preferred to carry out the reaction at a temperature of at least 100° C., in particular at least 140° C., in particular at least 170° C. On the other hand, higher temperatures may lead to the undesired formation of side products. It may therefore be preferred to carry out the reaction at a temperature of at most 350° C., in particular at most 280° C.

Depending on the reaction temperature, the reaction time can vary within wide ranges, e.g., between 15 minutes and 24 hours. It may be preferred for the reaction time to vary between 1 hour and 12 hours, in particular between 1 hour and 6 hours. When using lower amounts of base, longer reaction times may be required to obtain the desired degree of conversion.

Upon completion of the reaction, a reaction mixture will be obtained which contains ethyleneamines and a carbonate salt of the inorganic base. The salt can be removed by methods known in the art, e.g., by filtration where the salt is in solid form. An advantage of the process of the invention as compared to prior art processes is that less solid waste product is present in the product, which has to be removed.

The process according to the invention can be carried out in batch operation, fed-batch operation, or in a continuous operation, e.g., in a cascade of continuous flow reactor. Depending on the scale of the operation, continuous operation may be preferred.

As will be evident to the skilled person various embodiments of the present invention, and various preferences expressed herein can be combined as long as they are not mutually exclusive.

The present invention will be elucidated by the following examples, without being limited thereto or thereby.

EXAMPLES

Comparative Example 1: Conversion of Compound Mixture with NaOH 4.0 g of a mixture as represented by Table 1, 2.9 g NaOH (73 mmol, corresponding to 2.25 molar equivalents of NaOH per cyclic urea moiety) and 17.5 g water (970 mmol) were mixed in a pressure autoclave under an atmosphere of nitrogen. The mixture was heated at 220° C. for 2.5 h and was then allowed to cool. The mixture was analyzed by gas chromatography with flame ionization detector (GC-FID). The normalized analysis results are summarized in Table 1 below which shows that in total 31 wt-% L-TETA was present in the sample.

Example 2: Conversion of Compound Mixture with CO2 Removal Step Followed by NaOH Treatment 175 g of the same mixture as in Comparative Example 1, 570 g EDA (9.50 mmol), and 570 g water (31.7 mol) were mixed in a 2 L pressure vessel under an atmosphere of nitrogen. The reactor vessel was heated to 250° C. and when the temperature was around 235° C. a flow of nitrogen gas was applied. The nitrogen gas was introduced at the bottom of the reactor through a sparger (pore diameter 2 μm). A condenser was attached to the gas outlet of the reactor. The flow of nitrogen was around 1 L/min and the pressure was approximately 30 barg. The agitation speed was 250 rpm. The reactor was operated under these conditions for 6 hours before it was cooled down to room temperature. The sample was analyzed by GC-FID in the same way as in Comparative Example 1.

8.0 g of the intermediate mixture as obtained above (composition as in Table 1, entry 3), 1.9 g NaOH (47 mmol, corresponding to 2.25 molar equivalents of NaOH per cyclic urea moiety remaining after step 1) and 11.2 g water (622 mmol) were mixed in a pressure autoclave under an atmosphere of nitrogen. The mixture was heated at 220° C. for 2.5 h and was then allowed to cool. The mixture was analyzed by GC-FID. The composition is given in Table 1 below which shows that in total 44 wt-% L-TETA was present in the sample.

TABLE 1

| Description | Starting mixture | Product mixture of Comparative Example 1 | Intermediate mixture of Example 2 | Product mixture of Example 2 |
|---|---|---|---|---|
| reaction temperature (° C.) | 270 | 220 | 250 | 220 |
| reaction time (h) | 5.0 | 2.5 | 6.0 | 2.5 |
| EDA | 8 | 37 | 17 | 28 |
| EU | 33 | n.d | 8 | n.d |
| AEEA | n.d. | 14 | 9 | 11 |
| UAEEA | 13 | 0 | 1 | 1 |
| L-TETA | n.d. | 31 | 26 | 44 |
| Sum UTETAs | 38 | 7 | 22 | n.d. |

All GC-FID analysis results in wt-%
n.d. = below detection limit
Sum UTETAs denotes the sum of all L-TETA urea derivatives Direct treatment of a cyclic urea containing product mixture with NaOH afforded 31 wt-% L-TETA whereas 44 wt-% L-TETA was produced if the same product mixture was first treated with EDA and water under stripping conditions and then treated with less NaOH. In comparison to the direct caustic treatment of the starting mixture (Comparative Example 1) which used 0.725 g NaOH per g reaction mixture, subjecting the starting mixture to stripping conditions first (Example 2)—using water and EDA—it was possible to reduce the consumption of NaOH to 0.2375 g NaOH per g of intermediate mixture.

Example 3: Conversion of DUTETA

The feed used in this Example was DUTETA.

In a comparative example, DUTETA was mixed in a pressure autoclave under an atmosphere of nitrogen with a NaOH solution containing 13.2 mole water per mole NaOH, in an amount of 2.25 molar equivalents of NaOH per cyclic urea moiety. The mixture was heated at 220° C. for 2.5 h and was then allowed to cool. The product was analyzed by gas chromatography with flame ionization detector (GC-FID). The normalized results are summarized in Table 2 under the heading 3.1.

In the first step of an example according to the invention DUTETA and water (47 mole/mole U) were mixed in a 2 L pressure vessel under an atmosphere of nitrogen. The reactor vessel was heated to 270° C. and when the temperature was around 235° C. a flow of nitrogen gas was applied. The nitrogen gas was introduced at the bottom of the reactor through a sparger (pore diameter 2 μm). A condenser was attached to the gas outlet of the reactor. The flow of nitrogen was around 2 L/min and the pressure was approximately 30 barg. The agitation speed was 250 rpm. The reactor was operated under these conditions for 5 hours before it was cooled down to room temperature. The sample was analyzed by GC-FID. The normalized results are presented in Table 2 below under the heading 3.2.

The intermediate mixture as obtained above was mixed in a pressure autoclave under an atmosphere of nitrogen with an NaOH solution containing 13.2 mole water per mole NaOH, in an amount of 2.25 molar equivalents of NaOH per cyclic urea moiety. The mixture was heated at 220° C. for 2.5 h and was then allowed to cool. The product was analyzed by gas chromatography with flame ionization detector (GC-FID). The normalized analysis results are summarized in Table 2 under the heading 3.3.

TABLE 2

| Entry | 3.1 comparative | 3.2 intermediate mixture | 3.3 final mixture |
|---|---|---|---|
| PIP (wt %) | n.d. | n.d. | n.d. |
| AEP (wt %) | n.d. | 2.4 | 2.6 |
| DETA (wt %) | 2.0 | 1.7 | 3.5 |
| L-TEPA (wt %) | 2.0 | n.d. | 2.6 |
| U1TEPA (wt %) | 0.3 | 3.0 | 1.6 |
| L-TETA (wt %) | 87 | 24.4 | 70 |
| Sum UTETAs (wt %) | 0.7 | 62 | 9.1 |
| Conv to L-TETA (%) | 88 | 28 | 90 |
| NaOH/L-TETA (g) | 1.67 | x | 0.45 |

From a comparison of the product of the process according to the invention in 3.3 and the comparative product in 3.1 it can be seen that the process according to the invention shows a conversion of DUTETA to L-TETA which is at least the same (90% versus 88%), while using substantially less NaOH (0.45 g NaOH per g L-TETA produced versus 1.67 g NaOH per L-TETA produced).

Example 4 (Comparative): Conversion of DUTETA

To investigate the advantage of CO2 removal during the first step, a further comparative Example was carried out.

In the first step, DUTETA was treated with water as described in Example 3 above, except that the nitrogen sparger was not used, and that the reaction was carried out in a closed vessel. The normalized composition of the product is presented below in Table 3 under the heading 4.1.

The resulting product mixture was treated with a NaOH solution containing 13.2 mole water per mole NaOH, in an amount of 2.25 molar equivalents of NaOH per cyclic urea moiety under the conditions described in Example 3. The normalized composition of the resulting product is presented in Table 3 under the heading 4.2.

As the NaOH treatment did not result in sufficient conversion into L-TETA, the treatment was repeated using a fresh batch of NaOH solution. The normalized composition of the resulting product is presented in Table 3 under the heading 4.3.

As this second NaOH treatment again did not result in sufficient conversion into L-TETA, the treatment was again repeated using a fresh batch of NaOH solution. The normalized composition of the resulting product is presented in Table 3 under the heading 4.4.

TABLE 3

| | Entry | | | |
|---|---|---|---|---|
| | 4.1 | 4.2 | 4.3 | 4.4 |
| | Product of | Product of | Product of | Product of |
| | closed pot | first NaOH | second NaOH | third NaOH |
| Description | water treatment | treatment | treatment | treatment |
| PIP (wt %) | 2.7 | 1.2 | 0.93 | 1.1 |
| AEP (wt %) | 3.6 | 3.7 | 3.2 | 3.8 |
| DETA (wt %) | 2.5 | 4.3 | 5.4 | 7.2 |
| L-TEPA (wt %) | n.d. | 0.4 | 0.6 | 6.7 |
| U1TEPA (wt %) | 4.0 | 4.1 | 3.3 | n.d. |
| L-TETA (wt %) | 11.8 | 18.2 | 45.3 | 60.5 |
| Sum UTETAs (wt %) | 65.6 | 50.3 | 19.9 | n.d. |
| NaOH/L-TETA (g) | 1.03 | 0.84 | 0.85 | 1.56 |

As can be seen from Table 3, if the water treatment in the first step is carried out without CO2 removal, three treatments with NaOH are required to obtain a low UTETA content which is comparable with that obtained in the present invention. Also, relatively more side-products such as AEP, DETA, and L-TEPA are formed in Example 4.4 compared to Example 3.3. Slightly less NaOH (1.56 g NaOH/g L-TETA) is required than in the case that only an NaOH treatment is carried out, without pre-treatment with water, but considerably more NaOH is required as compared to the process according to the invention (Example 3.3)

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A process for converting cyclic alkyleneureas into their corresponding alkyleneamines, comprising:
in a first step, converting cyclic alkyleneureas into their corresponding alkyleneamines by reacting cyclic alkyleneureas in the liquid phase with water with removal of $CO_2$, so as to convert from about 5 mole % to about 95 mole % of alkyleneurea moieties in a feedstock to corresponding amines, wherein the corresponding alkyleneamines are triethylenetetramine, aminoethylethanolamine, and ethylenediamine, and
in a second step, adding an inorganic base and reacting cyclic alkylene ureas remaining from the first step with the inorganic base to convert the cyclic alkylene ureas completely or partially into corresponding alkyleneamines.

2. The process of claim 1, wherein the inorganic base has a pKb of less than 1.

3. The process of claim 1, wherein the feedstock comprises at least about 10 mole % of cyclic urea derivatives of alkyleneamine compounds comprising a —NH—$R_3$—NH—$R_3$—NH—$R_3$—NH— moiety, calculated on the total of cyclic urea compounds present in the mixture.

4. The process of claim 1, wherein the first step is carried out at a temperature of from about 150° C. to about 400° C.

5. The process of claim 1, wherein the first step is carried by reacting cyclic alkyleneureas in the liquid phase with water in an amount of from about 0.1 to about 20 mole water per mole urea moiety, at a temperature of at least about 230° C.

6. The process of claim 1, wherein the first step is carried out in the presence of an amine compound selected from the group of primary amines, cyclic secondary amines, and bicyclic tertiary amines.

7. The process of claim 1, wherein inorganic base is added in the second step in an amount of at least about 0.2:1 mole inorganic base per mole cyclic alkyleneurea moiety.

8. The process of claim 1, wherein in the second step the molar amount of cyclic ethylene urea moieties in the product provided to the treatment with the inorganic base is at most about 20:1.

9. The process of claim 1, wherein the second step is carried out at a temperature of from about 100° C. to about 350° C.

10. The process of claim 1, further comprising removing salt formed in the second step.

11. The process of claim 1, wherein the second step is carried out at a temperature of from about 170° C. to about 280° C.

12. The process of claim 1, wherein in the second step the molar amount of cyclic ethylene urea moieties in the product provided to the treatment with the inorganic base is at most about 5.5:1.

13. The process of claim 1, wherein in the second step the molar amount of cyclic ethylene urea moieties in the product provided to the treatment with the inorganic base is at most about 4:1.

14. The process of claim 1, wherein in the second step the molar amount of cyclic ethylene urea moieties in the product provided to the treatment with the inorganic base is at most about 3:1.

15. The process of claim 1, wherein inorganic base is added in the second step in an amount of at least about 2:1 mole inorganic base per mole cyclic alkyleneurea moiety.

16. The process of claim 1, wherein the first step is carried out at a temperature of from about 250° C. to about 320° C.

17. The process of claim 1, wherein the feedstock comprises at least about 20 mole % of cyclic urea derivatives of alkyleneamine compounds comprising a —NH—$R_3$—NH—$R_3$—NH—$R_3$—NH— moiety, calculated on the total of cyclic urea compounds present in the mixture.

* * * * *